(12) United States Patent
Karapetian

(10) Patent No.: US 11,950,773 B2
(45) Date of Patent: Apr. 9, 2024

(54) PLEDGETED TISSUE ANCHOR

(71) Applicant: Edwards Lifesciences Corporation, Irvine, CA (US)

(72) Inventor: Emil Karapetian, Huntington Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1074 days.

(21) Appl. No.: 16/418,643

(22) Filed: May 21, 2019

(65) Prior Publication Data

US 2019/0365368 A1 Dec. 5, 2019

Related U.S. Application Data

(60) Provisional application No. 62/677,260, filed on May 29, 2018.

(51) Int. Cl.
*A61B 17/04* (2006.01)
*A61F 2/24* (2006.01)
*A61B 17/00* (2006.01)

(52) U.S. Cl.
CPC ........ *A61B 17/0401* (2013.01); *A61F 2/2487* (2013.01); *A61B 2017/00876* (2013.01); *A61B 2017/0406* (2013.01); *A61B 2017/0427* (2013.01); *A61B 2017/0441* (2013.01); *A61B 2017/0464* (2013.01); *A61F 2220/0016* (2013.01)

(58) Field of Classification Search
CPC .................. A61F 2/2487; A61F 2/0063; A61F 2002/0072; A61B 17/0401; A61B 2017/0404; A61B 2017/0406; A61B 2017/0427; A61B 2017/0441; A61B 2017/0464; A61B 2210/0016
See application file for complete search history.

(56) References Cited

U.S. PATENT DOCUMENTS 4,823,794 A 4/1989 Pierce
5,219,359 A * 6/1993 McQuilkin ........... A61F 2/0036
606/232

(Continued)

FOREIGN PATENT DOCUMENTS

EP 1598018 A1 11/2005

*Primary Examiner* — Carrie R Dorna
(74) *Attorney, Agent, or Firm* — Fred Hale; CHANG & HALE LLP

(57) ABSTRACT

An anchoring system comprises a first anchoring device comprising a first attachment mechanism and a plugging device and a second anchoring device comprising a second attachment mechanism, each of the first anchoring device and the second anchoring device being configured to enter a tissue wall at a proximal side of the tissue wall, the first anchoring device being configured to exit the tissue wall through a first hole on a distal side of the tissue wall, the second anchoring device being configured to exit the tissue wall at a second hole on the distal side of the tissue wall, the first attachment mechanism configured to attach to the second attachment mechanism outside of the distal side of the tissue wall, and the plugging device configured to cover the first hole and fit between at least a portion of the first anchoring device and the distal side of the tissue wall.

13 Claims, 6 Drawing Sheets

(56) References Cited

U.S. PATENT DOCUMENTS

| | | | |
|---|---|---|---|
| 5,693,060 | A | 12/1997 | Martin |
| 6,506,197 | B1 | 1/2003 | Rollero et al. |
| 7,846,180 | B2 | 12/2010 | Cerier |
| 8,097,005 | B2 | 1/2012 | Cohn et al. |
| 8,439,976 | B2 | 5/2013 | Albertorio et al. |
| 8,918,193 | B2 | 12/2014 | Yacoubian |
| 9,011,487 | B2 | 4/2015 | Lindh, Sr. et al. |
| 2005/0283246 | A1 | 12/2005 | Cauthen et al. |
| 2006/0259074 | A1* | 11/2006 | Kelleher ............ A61B 17/0482 606/213 |
| 2010/0094425 | A1* | 4/2010 | Bentley ................ A61F 2/442 606/86 A |
| 2016/0270777 | A1 | 9/2016 | Miller et al. |
| 2019/0142587 | A1* | 5/2019 | Duffy .................... A61F 2/2436 623/2.11 |

\* cited by examiner

PLEDGETED TISSUE ANCHOR

RELATED APPLICATION

This application claims priority to U.S. Provisional Application No. 62/677,260, filed May 29, 2018, and entitled PLEDGETED TISSUE ANCHOR, the disclosure of which is hereby incorporated by reference in its entirety.

BACKGROUND

Field

The present disclosure generally relates to the field of tissue anchors.

Description of Related Art

Many clinical therapies involve the use of tissue anchors. For example, tissue anchors can be anchored into ventricular tissue for attaching valves, plugging devices, approximating papillary muscles, remodeling the ventricle, etc.

SUMMARY

In some implementations, the present disclosure relates to an anchoring system that may be minimally invasive and may reduce risk of failure and bleeding in some cases. In accordance with some embodiments, the anchoring system comprises a first anchoring device, a second anchoring device, and a plugging device. The first anchoring device comprises a first attachment mechanism and the second anchoring device comprises a second attachment mechanism. Each of the first anchoring device and the second anchoring device is configured to enter a tissue wall at a proximal side of the tissue wall. The first anchoring device is configured to exit the tissue wall through a first hole on a distal side of the tissue wall and the second anchoring device is configured to exit the tissue wall at a second hole on the distal side of the tissue wall. The first attachment mechanism is configured to attach to the second attachment mechanism outside of the distal side of the tissue wall. The plugging device may extend from and/or be attached to the first anchoring device or second anchoring device and is configured to at least partially cover the first hole and fit between at least a portion of the first anchoring device and the distal side of the tissue wall.

The first anchoring device may comprise a suture, the first attachment mechanism may be situated near an end portion of the suture, and the plugging device may be attached to the suture. The plugging device may be configured to lay flat against the suture while inside the tissue wall and extend perpendicularly from the suture after exiting the tissue wall. The plugging device may be at least partially composed of felt and the first anchoring mechanism may comprise at least one of a barb, a magnet, a hook, a lasso, a corkscrew, a peg, and a tie. The first anchoring device may be configured to puncture the proximal side of the tissue wall. The plugging device may be configured to fit between at least a portion of the second anchoring device and the distal side of the tissue wall and may be configured to at least partially cover the second hole.

In some implementations, the present disclosure relates to an anchoring system comprising a first anchoring device and a second anchoring device. The first anchoring device comprises a first attachment mechanism and the second anchoring device comprises a second attachment mechanism. Each of the first anchoring device and the second anchoring device is configured to enter a tissue wall at a proximal side of the tissue wall. At least a portion of the first anchoring device is configured to exit the tissue wall through a first hole on a distal side of the tissue wall and at least a portion of the second anchoring device is configured to exit the tissue wall through a second hole on the distal side of the tissue. The first attachment mechanism is configured to attach to the second attachment mechanism outside of the distal side of the tissue wall and the second attachment mechanism is configured to at least partially cover the first hole to prevent bleeding.

The second attachment mechanism may be further configured to fit between at least a portion of the first anchoring device and the distal side of the tissue wall and may be at least partially composed of metal and cloth. The first attachment mechanism may comprise a corkscrew or a barb.

The anchoring system may further comprise a third anchoring device comprising a third attachment mechanism. The third anchoring device may be configured to enter the tissue wall at the proximal side of the tissue wall. At least a portion of the third anchoring device may be configured to exit the tissue wall through a third hole on the distal side of the tissue wall and the third attachment mechanism may be configured to attach to the second attachment mechanism outside of the distal side of the tissue wall. The second attachment mechanism may be configured to at least partially cover the third hole to prevent bleeding. The third attachment mechanism may comprise a corkscrew or a barb.

In some implementations, the present disclosure relates to a method for anchoring to a tissue wall. The method comprises delivering a catheter into close proximity of the tissue wall and passing a first anchoring device through the catheter. The first anchoring device comprises a first attachment mechanism. The method further comprises passing a second anchoring device through the catheter. The second anchoring device comprises a second attachment mechanism. The method further comprises inserting the first anchoring device into a proximal side of the tissue wall such that at least a portion of the first attachment mechanism protrudes from a distal side of the tissue wall and inserting the second anchoring device into the proximal side of the tissue wall such that at least a portion of the second attachment mechanism protrudes from the distal side of the tissue wall. The method further comprises connecting the first attachment mechanism to the second attachment mechanism outside the distal side of the tissue wall.

The first anchoring device may be configured to protrude from a first hole in the distal side of the tissue wall and the second attachment mechanism may be configured to at least partially cover the first hole to prevent bleeding. The second attachment mechanism may be configured to fit between at least a portion of the first anchoring device and the distal side of the tissue wall. The first anchoring device further may comprise a plugging device. The first anchoring device may be configured to protrude from a first hole in the distal side of the tissue wall and the plugging device may be configured to at least partially cover the first hole to prevent bleeding. The third attachment mechanism may comprise a corkscrew or a barb.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
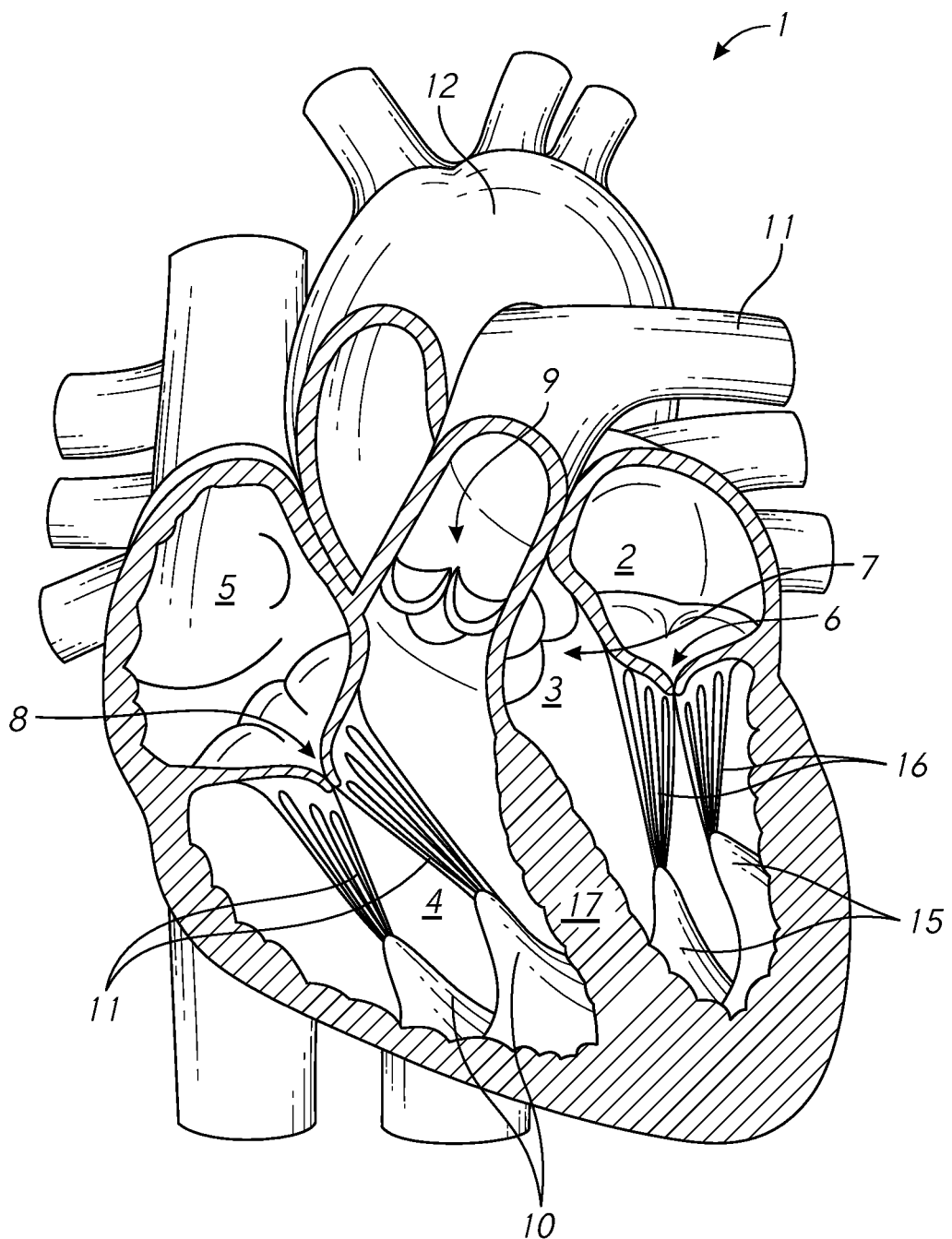
FIG. 1 provides a cross-sectional view of a human heart.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

The present disclosure provides systems, devices, and methods relating to tissue anchors and other tissue-piercing/penetrating devices, which may be used for certain medical procedures, or for other applications. Devices disclosed herein may be designed or configured to be embedded in, or otherwise attached to, biological tissue. However, it should be understood that principles disclosed herein may be applicable to devices and methods for embedding or securing to non-biological tissue as well. In some embodiments, the present disclosure and corresponding figures relate to anchoring devices with specific attachment mechanisms, such as magnets, corkscrews, and barbs. However, it should be understood that the disclosed principles may be applicable to other types of tissue anchors or tissue-piercing devices (e.g., hypodermic needles or tubes, or the like). Therefore, description herein of anchors comprising a particular type is applicable to other types of anchors and devices as well.

Tissue anchors may be used to attach or anchor to biological tissue. For example, in connection with certain cardiac procedures, tissue anchors or the like may be used to embed in or otherwise secure to cardiac anatomy, which may be useful for various therapies. For example, cardiac resynchronization therapy (CRT), percutaneous angioplasty, or other therapies or medical or cardiac procedures may utilize tissue anchors and other tissue-puncturing devices in some implementations.

For convenience, in some contexts, the present disclosure describes embodiments in the context of cardiac operations. However, it should be understood that the disclosed embodiments may be implemented in connection with any type of medical procedure. To provide context for the disclosure herein relating to cardiac operations, FIG. 1 and the associated description show and describe a human heart. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11 and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant, and press back against the leaflets. As a result, the leaflets/cusps come in apposition to each other, thereby closing the flow passage.

The atrioventricular (i.e., mitral and tricuspid) heart valves may further comprise a collection of chordae tendineae and papillary muscles for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles by the chordae tendineae 11, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle adjustment disclosed herein are applicable to atrioventricular valves having any number of leaflets and/or papillary muscles associated therewith.

The right ventricular papillary muscles 10 originate in the right ventricle wall, and attach to the anterior, posterior and septal leaflets of the tricuspid valve, respectively, via the chordae tendineae 11. The papillary muscles 10 of the right ventricle 4 may have variable anatomy; the anterior papillary may generally be the most prominent of the papillary muscles. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. The various chords of the chordae tendineae may have different thicknesses, wherein relatively thinner chords are attached to the free leaflet margin, while relatively thicker chords (e.g., strut chords) are attached farther away from the free margin.

Pledgeted Tissue Anchors

Many clinical therapies involve the use of tissue anchors. For example, tissue anchors can be anchored into ventricular tissue for attaching to valves or plugging devices, approximating papillary muscles, remodeling the ventricle, and other uses. In some embodiments, an anchor may be attached to a tensioning element, such as a suture or the like, that applies a pulling force to the anchor. The term "tensioning element" is used herein according to its broad and ordinary meaning, and may refer to any type of suture, line, strand, string, spring, tie, strap, of other component or material configured to provide tensioning or securing force between two points. The anchor in turn applies a pulling force to the tissue. Some tissue anchors are configured to apply force to the tissue at a single point. For example, certain anchoring methods involve puncturing a single hole in a tissue wall and inserting an anchoring device into the wall. The anchoring device may be, for example, a balloon device that expands within the wall and is configured to apply a pulling force to the punctured tissue wall. When a pulling force is applied to the anchor, a substantial portion of the force (e.g., approximately the entire applied force) can in turn be applied at the tissue wall at a point where the anchor is in contact with the tissue wall (e.g., around the point of the hole in the tissue wall). Such implementations may inherently produce a relatively weak anchor in compliant tissues because, as pulling force is applied to the anchor within the tissue wall, the tissue may form a funnel-like shape, and the anchor may at least partially become squeezed through at least a portion of the hole in the tissue wall and/or break through or otherwise damage the tissue surrounding the hole in the tissue wall.

Figure 2:
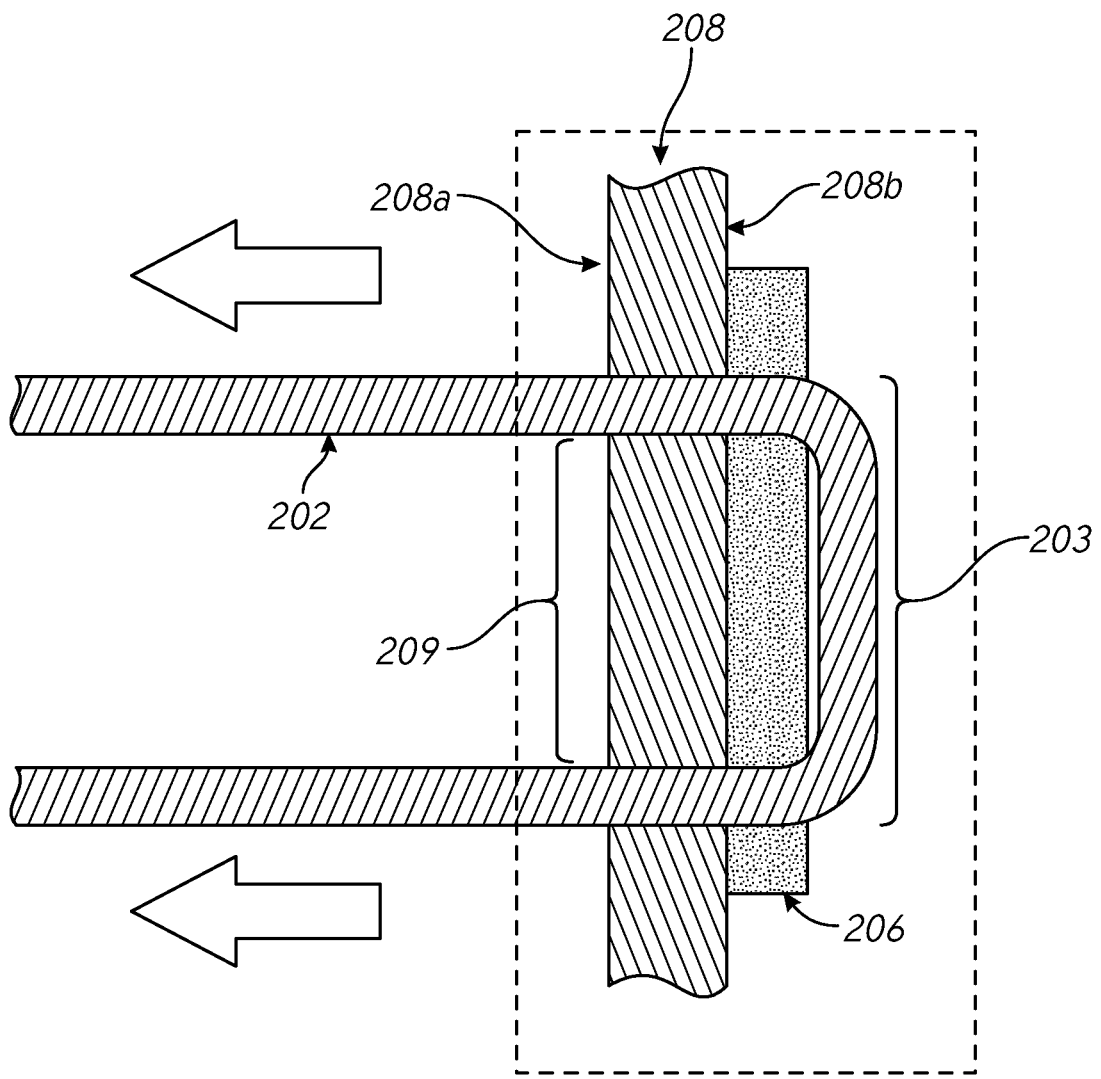
FIG. 2 provides a perspective view of a multi-point pledgeted tissue anchor in accordance with one or more embodiments.

Other anchoring methods involve the use of multi-point anchors, which may be configured to spread a pulling force across an area of tissue between multiple insertion points. FIG. 2 illustrates a multi-point pledgeted tissue anchor in accordance with one or more embodiments. The anchor comprises a suture 202 which passes entirely through a tissue wall 208 at multiple points. As used herein, the term "suture" is used according to its plain and ordinary meaning and may refer to any elongate strip, strand, line, tie, string, ribbon, strap, or other type of material used in medical procedures. One having ordinary skill in the art will understand that a wire or other similar material may be used in place of a suture.

The suture 202 may pass entirely through the tissue wall 208 and extend perpendicularly, or near-perpendicularly, beyond both a proximal side 208*a* and a distal side 208*b* of the tissue wall 208. A distal portion 203 of the suture 202 may be exposed on the distal side 208*b* of the tissue wall 208. The distal portion 203 may extend along an enclosed portion 209 of the tissue wall 208 on the distal side 208*b* of the tissue wall 208. The distal portion 203 may have any length. For example, in some embodiments, the distal portion 203 of the suture is between zero and ten millimeters in length. A pledget 206 or similar device may be configured to fit between the distal portion 203 and the distal side 208*b* surface of the tissue wall 208. As used herein, the term "pledget" is used according to its plain and ordinary meaning and may refer to any at least partially compressible and/or soft or absorbent biocompatible pad or material used in medical procedures. The pledget 206 may be attached to the suture 202 in a form similar to an Amplatzer™ or other similar device, in which the pledget 206 may be configured to lay substantially flat against, or relative to, the suture 202 during insertion through the tissue wall, and after exiting the tissue wall may extend perpendicularly from the proximal portion of the suture 202, and further lay substantially flat against the distal side 208b surface of the tissue wall 208. In an embodiment, the pledget 206 may be at least partially composed of felt or a similar material. The pledget 206 may have suitable or desirable thickness, length, and width, and further may be at least partially compressible or expandable in one or more dimensions. In an embodiment, one or more of the thickness, length, and/or width of the pledget 206 may exceed a respective thickness, length, and/or width, respectively, of the distal portion 203 of the suture 202. The suture 202 may pass through holes or gaps in the pledget 206 in some embodiments. In some embodiments, the pledget 206 may not extend beyond the enclosed portion 209 of the tissue wall 208 in one or more directions/dimensions.

A pledgeted suture anchor as illustrated in FIG. 2 may have several advantages over single-point tissue anchors. First, the suture 202 may pass through the entire tissue wall 208, and the suture 202 may extend along the enclosed portion 209 of the distal side 208b of the tissue wall 208. In this way, as pulling force is applied to the suture 202, force may be applied along substantially the entire enclosed portion 209 of the tissue wall 208. As such, the suture 202 would generally have to cut through the enclosed portion 209 of the tissue wall 208 to fail. The amount of force required to cut through the enclosed portion 209 of the tissue wall 208 may be much higher than an amount of force required to pull an anchor through a single hole or attachment point as in a single-point anchor. Accordingly, the pledgeted suture anchor may be particularly useful when a high load may be placed on the suture 202.

Moreover, in single-point anchors, force caused by high loads may cause stress around an insertion point of the anchor, and may result in damage to the surrounding tissue. Accordingly, another advantage of the pledgeted suture anchor is that the pledget 206 increases the surface area contact of the suture 202, and any resulting stress caused by force on the suture 202 may be at least partially spread across the distal portion 203 of the suture 202. In this way, use of a pledgeted suture anchor similar to the suture anchor shown if FIG. 2 may reduce damage to the tissue wall 208 by preventing excessive stress at any one point of the tissue wall 208.

Another advantage of the pledgeted suture anchor is that the pledget 206 may be configured to plug holes in the tissue wall to prevent bleeding. For example, in some implementations, piercing through a ventricular wall can introduce a risk of development of cardiac tamponade and/or other conditions due to the possibility of bleeding at the puncture point(s) in the tissue wall 208. The placement of the pledget 206 adjacent to and/or surrounding the suture 202 may create an at least partial seal over the hole(s) introduced in the tissue wall 208. The pledget 206 may comprise an absorbent or similar material, and may be configured to minimize the risk or occurrence of bleeding.

A delivery system for the pledgeted suture anchor illustrated in FIG. 2 may involve accessing both sides of the tissue wall 208. For example, an end of the suture 202 may be inserted through a first hole in the tissue wall 208 at the proximal side 208a using a catheter. The suture 202 may then be passed through the tissue wall 208 and exit through a second hole on the distal side 208b. In order to access the end of the suture 202 while on the distal side 208b of the tissue wall 208, a surgeon may insert a second catheter or other device to provide access to the distal side 208b of the tissue wall 208. By accessing the distal side 208b of the tissue 208 wall, the suture 202 may be re-inserted into the tissue wall 208 at a second point on the distal side 208b of the tissue wall 208. In some cases, accessing the distal side 208b of the tissue wall 208 may involve invasive procedures or may not be possible in some circumstances.

Some embodiments described herein advantageously provide systems and methods for multi-point anchors that may be anchored to a tissue wall while accessing only a first (e.g., proximal) side of the tissue wall. In some embodiments, a multi-point anchor is achieved by advancing multiple anchoring devices (e.g., sutures or similar devices) through one or more delivery catheters to bring the anchoring device(s) into close proximity of a first side of a tissue wall. The multiple anchoring devices may each be inserted through the tissue wall, but may pass through different holes, or passages, in the tissue wall and surface at different points on a distal side of the tissue wall. The multiple anchoring devices may connect to each other and/or connect to a common object (e.g., a pledget or other plugging device) on the distal side of the tissue wall. In this way, the multiple anchoring devices can create a multi-point anchor that is capable of insertion with access to only a single side of the tissue wall. Therefore, methods of inserting multi-point anchors as described herein may provide minimally invasive solutions, and implementations thereof may be possible even when a distal side of the target tissue wall is not accessible. When attached on the distal side of the tissue wall, the multiple anchoring devices may respond to proximal force as a single device. Accordingly, pulling force applied to any of the anchoring devices may be at least partially spread across one or more additional anchoring devices.

A plugging device or mechanism may be attached to and/or extend from an anchoring device, or may be inserted separately from the anchoring devices. The plugging device may be configured to fit between one or more of the anchoring devices and the tissue wall such that force applied to the anchoring devices may be spread at least partially across the plugging device/mechanism. Moreover, the plugging device may be configured to at least partially cover holes in the tissue wall to prevent bleeding. The plugging device may be inserted from the proximal side of the tissue wall and may be configured to extend or expand (e.g., unfold) on the distal side of the tissue wall. In this way, the plugging device may be placed on the distal side of the tissue wall from a delivery point on the proximal side of the tissue wall.

Multi-Point Anchor Delivery Systems

Figure 3:
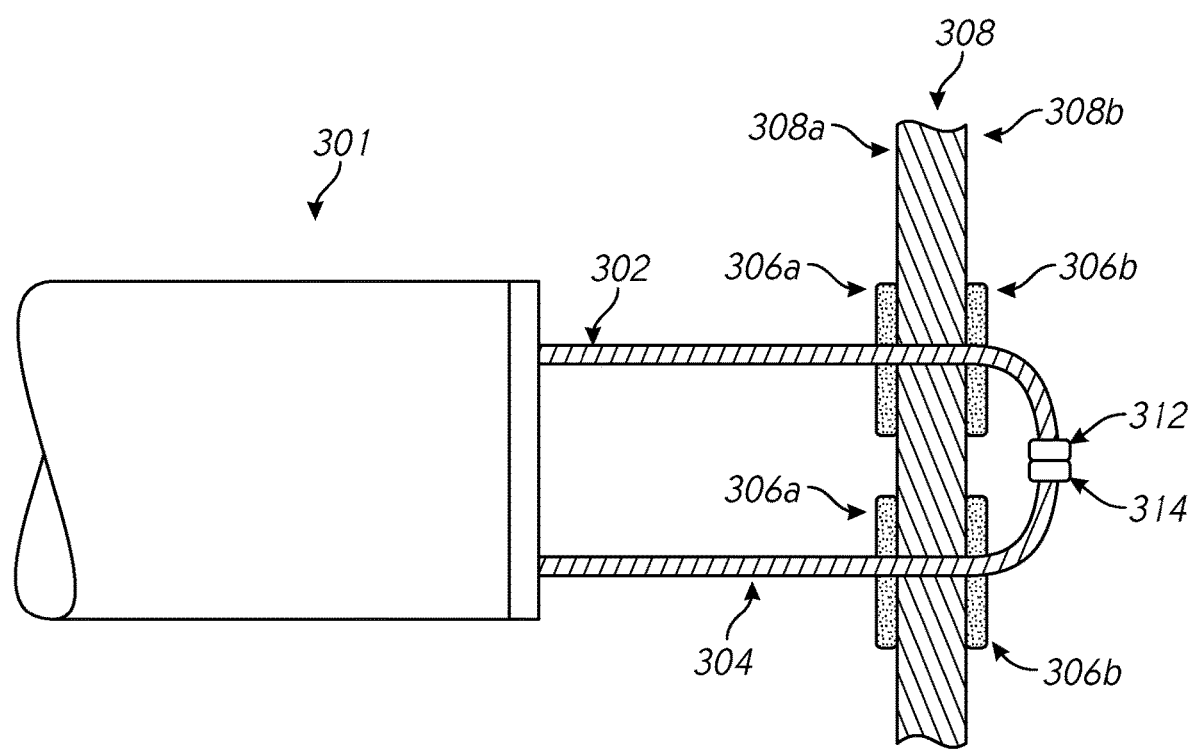
FIG. 3 illustrates a delivery system for a multi-point pledgeted tissue anchor via a catheter in accordance with one or more embodiments.

FIG. 3 illustrates a delivery system for inserting a multi-point anchor via a catheter 301 in accordance with one or more embodiments. A catheter 301 may be inserted into a patient's body such that an end of the catheter 301 may be brought or advanced into close proximity to a first side 308a of a tissue wall 308. A first anchoring device 302 may be inserted through the catheter 301. The first anchoring device 302 may pass through the tissue wall 308 at a first point in the tissue wall 308. In some embodiments, the first anchoring device 302 may puncture the first side 308a of the tissue wall 308, while in other embodiments, the first anchoring device 302 may pass through an existing hole in the tissue wall 308. For example, a puncturing device may be utilized to first create a hole in the tissue wall 308 and the anchoring device 302 may be inserted through the hole. A second anchoring device 304 may also be provided using the catheter 301. Although both the first anchoring device 302 and the second anchoring device 304 are shown in FIG. 3 as being provided using a common catheter 301, the second anchoring device 304 may alternatively be provided using a separate catheter and/or other delivery device. The first anchoring device 302 and second anchoring device 304 may be implanted simultaneously or may be implanted at different times. The second anchoring device 304 may pass through the tissue wall 308 at a second point of the tissue wall 308, which may be separated from the first point by a few millimeters or any other distance.

The first anchoring device 302 may comprise a first connector 312. The term "connector" is used herein according to its broad and ordinary meaning, and may refer to any component, device, mechanism, or feature configured to be joined with, or attached or secured to, another device, component, mechanism, or feature, or component or portion thereof, or to biological tissue or portion thereof. The first connector 312 may extend from and/or may be attached at or near an end of the first anchoring device 302. The second anchoring device 304 may comprise a second connector 314 at or near an end portion of the second anchoring device 304. The first connector 312 may be configured to connect with the second connector 314 on a distal side 308b of the tissue wall 308. For example, the first connector 312 and the second connector 314 may comprise magnets that may be configured to magnetically and/or physically couple to each other when placed in sufficiently close proximity. In another example, the first connector 312 may comprise a loop or lasso and the second connector 314 may comprise a hook or other device configured to connect to the loop or lasso, or vice versa. In other examples, each of the first connector 312 and the second connector 314 may comprise any type of mechanical connectors configured to connect or be otherwise attached or secured to one another when placed in sufficiently close proximity with each other, or when coupled together in some manner. When connected, the first connector 312 and the second connector 314 may create a connection between the first anchoring device 302 and the second anchoring device 304 such that the first anchoring device 302 and second anchoring device 304 together may function as a singular device. Accordingly, when a force is applied to either the first anchoring device 302 or the second anchoring device 304 (or both simultaneously), both the first anchoring device 302 and the second anchoring device 304 may apply resistive force. Moreover, force applied to the first anchoring device 302 and/or second anchoring device 304 may be spread at least partially along portions of both the first anchoring device 302 and the second anchoring device 304 that may be disposed on the distal side 308b of the tissue wall 308.

One or more plugging devices 306a, 306b (e.g., pledgets) may be attached to the tissue wall. In some embodiments, the one or more plugging devices 306a, 306b may extend from and/or be connected to the first anchoring device 302 and/or second anchoring device 304. One or more proximal plugging devices 306a may be situated or disposed on the proximal side 308a of the tissue wall 308 and one or more distal plugging devices 306b may be situated or disposed on the distal side 308b. The proximal plugging device(s) 306a may be separate or may be combined into a single form or device (e.g., a pledget). Similarly, the distal plugging device(s) 308b may be separate or may be combined into a single form or device (e.g., a pledget). Any of the one or more plugging devices 306a, 306b may be removed and/or may not be included. The distal plugging devices 308b may be configured to increase surface area of force when a pulling force is applied to the first anchoring device 302 and/or second anchoring device 304. Each of the one or more plugging devices 306a, 306b may be configured to at least partially cover and/or create a seal around the first anchoring device 302 and/or second anchoring device 304 to prevent bleeding at holes or openings in the tissue wall 308.

At least a portion of the distal plugging devices 306b may be configured to fit between the first anchoring device 302 and/or second anchoring device 304 (on one side) and the distal side 308b of the tissue wall 308 (on a second side). The plugging devices 306a, 306b may be at least partially composed of an absorbent material (e.g., cotton, felt, or the like). Either of the anchoring devices 302, 304 may be sutures or similar devices. While two anchoring devices 302, 304 are shown, additional anchoring devices could be included.

Figure 4:
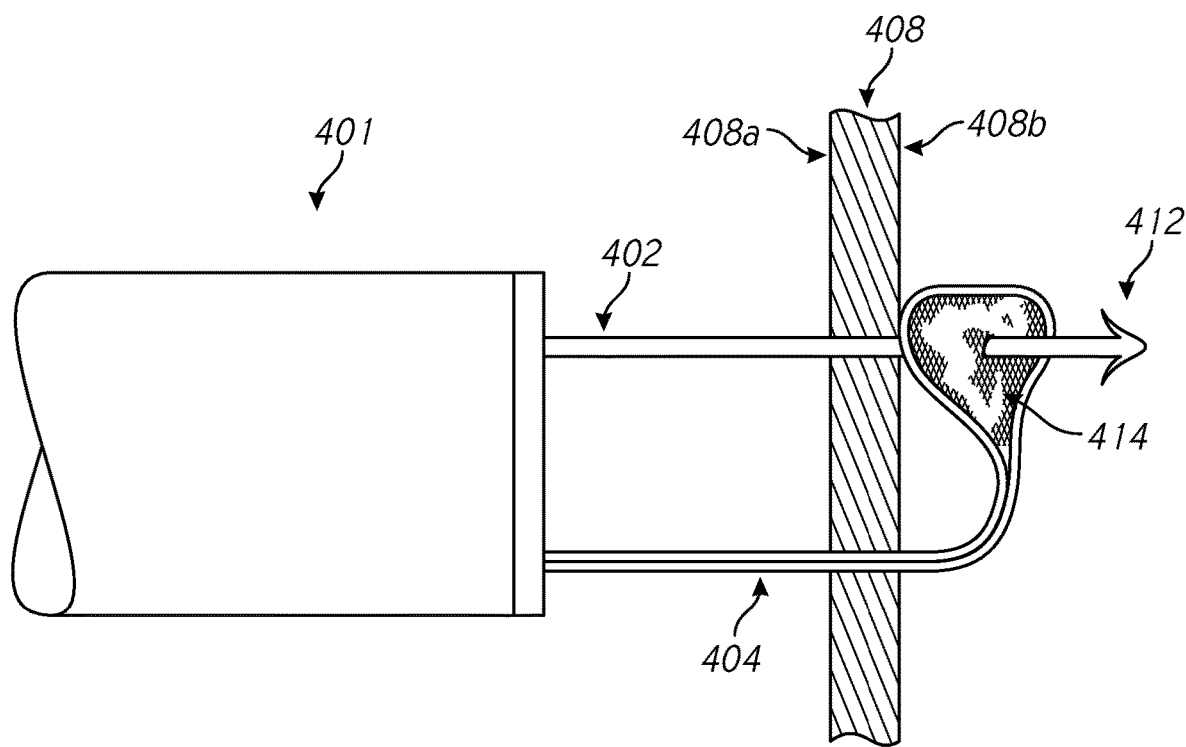
FIG. 4 illustrates a delivery system for a multi-point pledgeted tissue anchor via a catheter in accordance with one or more embodiments.

FIG. 4 illustrates another delivery system for a multi-point anchor via a catheter in accordance with one or more embodiments. As shown in FIG. 4, a catheter 401 may be inserted into a patient's body and advanced and approximated to a target tissue wall 408 to provide access to a proximal side 408a of the tissue wall 408.

A first anchoring device 402 may be deployed from the catheter 401 and passed through the tissue wall 408 at a first point in the tissue wall 408. A second anchoring device 404 may also be deployed from the catheter 401, or from a separate catheter or other delivery device, and passed through the tissue wall 408 at a second point in the tissue wall. The first anchoring device 402 and/or second anchoring device 404 may puncture the tissue wall 408 and/or may be inserted through existing holes or openings in the tissue wall 408. The first anchoring device 402 and/or second anchoring device 404 may be provided from the catheter 401 at different times or at or around the same time. The first point and second point of the tissue wall may be separated by a few millimeters or a greater distance.

The first anchoring device 402 may comprise a first attachment feature 412 at or near an end portion, or different portion, of the first anchoring device 402. The second anchoring device 404 may comprise a second attachment feature 414 at an end portion, or different portion, of the second anchoring device 404. The second attachment feature 414 may comprise, for example, a section or portion of cloth and/or a mesh composed of wire, polymer, or other suitable material. For example, in some embodiments, the second attachment feature 414 may comprise a metallic mesh overlaid with cloth or similar material. The first attachment feature 412 may be any mechanism suitable for connecting to and/or passing through the second attachment feature 414 to create a connection between the first anchoring device 402 and the second anchoring device 404. For example, the first attachment feature 412 may comprise one or more barbs configured to pierce through and hook into the second attachment feature 414. The first attachment feature 412 may alternatively comprise a corkscrew anchor, balloon anchor, and/or other suitable anchoring feature or mechanism.

The second attachment feature 414 may have features similar to a pledget or other plugging device, and may be configured to at least partially create a seal around a portion of the first anchoring device 402 to cover and/or plug one or more holes or openings in the tissue wall 408. When connected to the first anchoring device 402, the second anchoring device 404 may be situated such that the second attachment feature 414 fits between at least a portion of the first anchoring mechanism 412 and the distal side 408b of the tissue wall 408. Accordingly, the first attachment feature 412 may be configured to press against the second attachment feature 414 such that the second attachment feature 414 maintains contact with the distal side 408b of the tissue wall 408. When a pulling force is applied to the first anchoring device 402 and/or second anchoring device 404, the first attachment feature 412 and/or second attachment feature 414 may apply a force across an area of the distal side 408b of the tissue wall. For example, the applied force may be at least partially spread across the second attachment feature 414.

The second attachment feature 414 may be configured to be moveable between a collapsed form and an expanded form. For example, when inserted through the tissue wall 408, the second attachment feature 414 may collapse to fit through a hole in the tissue wall. After exiting the tissue wall 408 on the distal side 408b thereof, the second attachment feature 414 may expand to cover a greater surface area.

In certain embodiments, the second anchoring device 404 may first be inserted through the tissue wall 408. After the second attachment feature 414 is in place on the distal side 408b of the tissue wall 408, the first anchoring device 402 may be passed through the tissue wall 408 such that the first attachment feature 412 penetrates and/or otherwise attaches to the second attachment feature 414.

Figure 5:
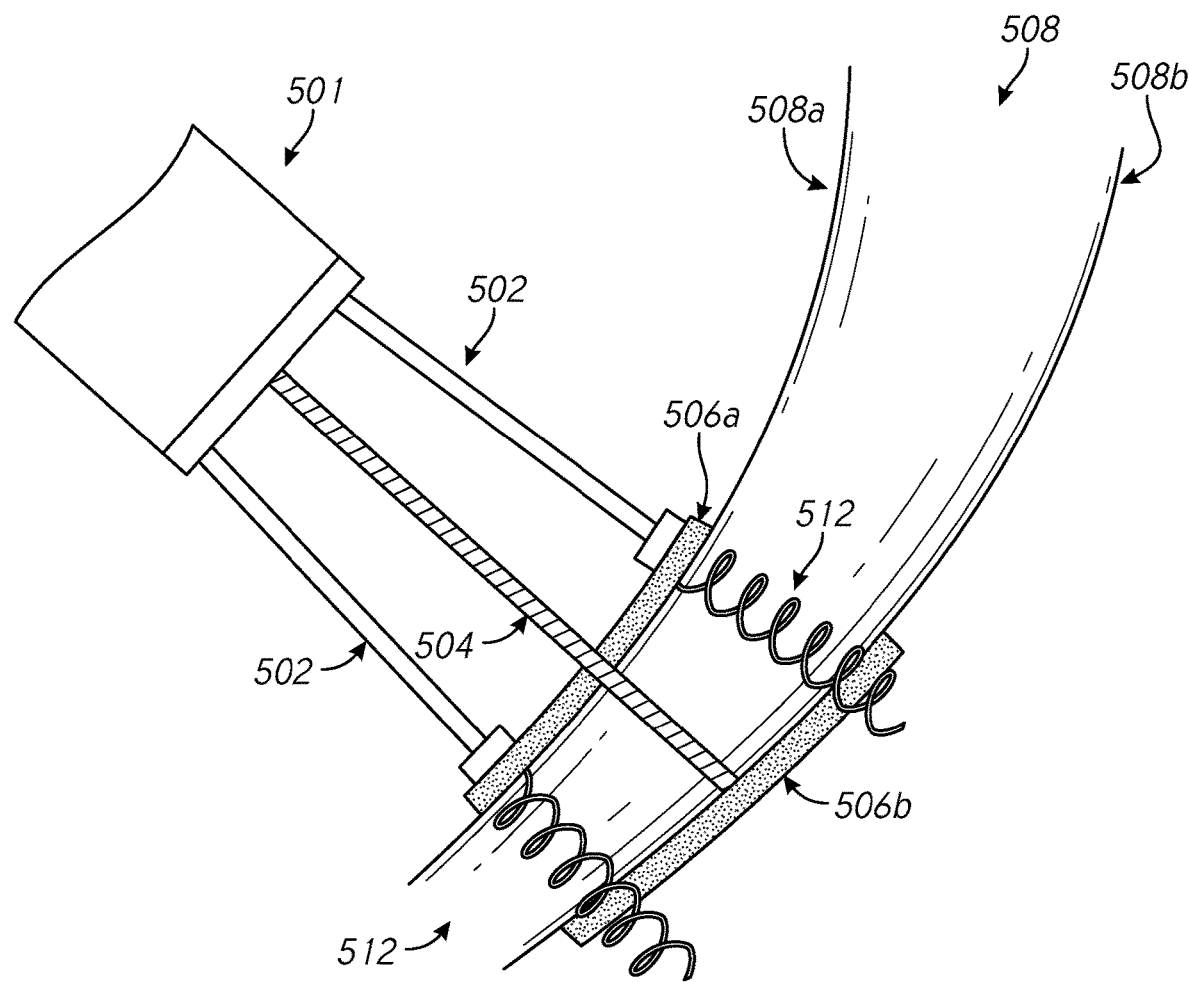
FIG. 5 illustrates a delivery system for a multi-point pledgeted tissue anchor via a catheter in accordance with one or more embodiments.

FIG. 5 illustrates another system for delivering a multi-point anchor via a catheter in accordance with one or more embodiments. As shown in FIG. 5, a catheter 501 may be inserted into a patient's body to provide access to a proximal side 508a of a tissue wall 508.

A type-one anchoring device 504 may be passed through the catheter 501. The type-one anchoring device 504 may comprise a type-one attachment device or feature 506a and/or a type-two attachment device or feature 506b. Each of the type-one attachment device 506a and the type-two attachment device 506b may comprise a pledget or other plugging device and may be at least partially composed of felt, cotton, or other suitable material. The type-one anchoring device 504 may be passed through a first point of the tissue wall 508. The type-one anchoring device 504 may comprise an Amplatzer™ or other similar mechanism for folding and expanding the type-one attachment device 506a and/or type-two attachment device 506b. For example, during insertion of the type-one anchoring device 504, the type-two attachment device 506b may be in a folded or compacted state. After the type-two attachment device 506b exits the distal side 508b of the tissue wall 508, the type-two attachment device 506b may unfold or expand to cover a greater surface area on the distal side 508b of the tissue wall 508. A type-one attachment device 506a may be configured to lay flat against the proximal side 508a of the tissue wall 508.

One or more type-two anchoring devices 502 may be provided through the catheter 501. The one or more type-two anchoring devices 502 may be passed through the tissue wall 508 at different points/areas of the proximal side 508a of the tissue wall 508. Each of the one or more type-two anchoring devices 502 may comprise a type-three attachment device 512. The type-three attachment devices 512 may be any mechanisms suitable for connecting to the type-one attachment device 506a and/or the type-two attachment device 506b. For example, the type-three attachment devices 512 may comprise corkscrews, barbs, hooks, screws, or other devices. In some embodiments, the type-three attachment devices 512 may anchor into at least a portion of the type-one attachment device 506a, the tissue wall 508, and/or the type-two attachment device 506b.

The type-one attachment device 506a may be configured to at least partially cover and/or plug holes or openings in the proximal side 508a of the tissue wall 508. The type-one attachment device 506a may further be configured to fit between at least a portion of a type-two anchoring device 502 and the proximal side 508a of the tissue wall 508. The type-three attachment devices 512 may be configured to penetrate the type-one attachment device 506a or may pass through existing holes in the type-one attachment device 506a. Similarly, the type-three attachment devices 512 may be configured to penetrate or pass through existing holes in the second attachment device 512. The type-two attachment device 506b may be configured to at least partially cover and/or plug holes in the distal side 508b of the tissue wall 508.

In certain embodiments, the type-one anchoring device 504 may be first inserted through the catheter 501. After the type-one anchoring device 504 is in place, the type-two anchoring devices 502 may be inserted and may attach to the type-one anchoring device 504.

In some embodiments, the type-one attachment devices 506a and/or the type-two attachment device 506b may comprise multiple materials and/or multiple densities of a single material. For example, a portion of the type-two attachment device 506b may comprise a hardened and/or dense material to prevent the type-three attachment devices 512 from passing through such portion. For example, the portion may be an area of the type-two attachment device 506b that is distal from an entry point of the type-three attachment devices 512 such that the type-three attachment devices 512 can be partially inserted into the type-two attachment device 506b but the type-three attachment devices 512 may be prevented from passing entirely through the type-two attachment device 506b.

While two type-two anchoring devices 502 are shown, a single type-two anchoring device 502 or more than two type-two anchoring devices 502 may be used. Each of the type-two anchoring devices 502 may attach to the type-one anchoring device 504 and/or another anchoring device.

In some embodiments, a multi-point anchor as described herein may be configured to reshape at least a portion of a tissue wall. For example, the multi-point anchor of FIG. 5 may comprise two or more type-two anchoring devices 502. The type-two anchoring devices 502 may have varying lengths or may be otherwise configured to apply a stronger pulling force to some portions of the tissue wall 508 than to other portions of the tissue wall 508. As a result of the pulling force, the tissue wall 508 may gradually change shape over time.

Anchor Delivery Processes

Figure 6:
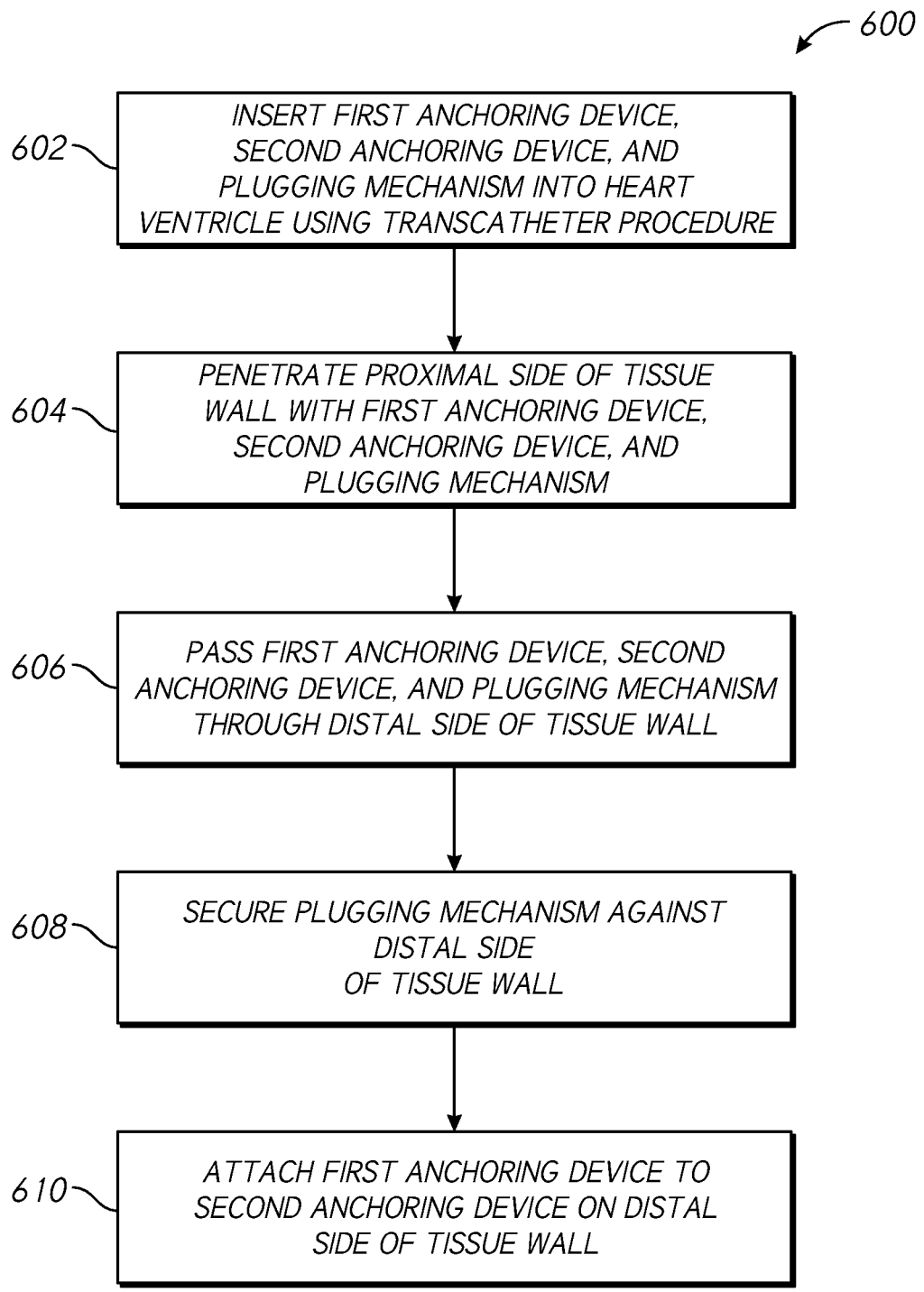
FIG. 6 is a flow diagram representing a process for delivering a multi-point anchor in accordance with one or more embodiments.

FIG. 6 is a flow diagram representing a process 600 for delivering a multi-point anchor according to one or more embodiments disclosed herein.

At block 602, the process 600 involves inserting a first anchoring device, a second anchoring device, and one or more plugging devices into a patient's body using a trans-catheter procedure, or the like. For example, a catheter may be inserted into the right or left ventricle of the patient's heart. The catheter may be positioned such that an opening of the catheter is in close proximity to a proximal side of a tissue wall. The positioning of the catheter may allow access by a surgeon to the proximal side of the tissue wall. The "proximal side" of the tissue wall may be a side of the tissue wall that is closest to an opening of the catheter. A side of the tissue wall that is further from the opening of the catheter than the proximal side may be referred to as a "distal side" of the tissue wall. The catheter may provide direct access to a proximal side of the tissue wall but may not provide direct access to a distal side of the tissue wall. For example, the first anchoring device, second anchoring device, and plugging device, when passed through the catheter, may not be able to contact the distal side of the tissue wall without piercing through the tissue wall.

The first anchoring device and/or second anchoring device may be any devices and/or may comprise any mechanisms suitable for anchoring into a tissue wall and connecting to another anchoring device. For example, the first anchoring device and/or second anchoring device may comprise a corkscrew, balloon, hook, barb, magnet, and/or any other mechanism.

In some embodiments, the plugging device or multiple plugging devices may be attached to, may extend from, or may otherwise be connected to the first anchoring device and/or second anchoring device. Multiple plugging devices may be attached to different points on an anchoring device. A plugging device may be moveable such that the plugging device may be held flat against an anchoring device during insertion into the tissue wall and may expand to lay flat against the distal side of the tissue wall after protruding from the distal side of the tissue wall. In some embodiments, one or more plugging devices may be inserted separately from the first and/or second anchoring device. For example, after a plugging device is placed on the distal side of the tissue wall, the first anchoring device and/or second anchoring device may be inserted through the tissue wall and may pierce through the plugging device.

At block 604, the process 600 involves penetrating a proximal side of a tissue wall with the first anchoring device, second anchoring device, and plugging device. The first anchoring device, second anchoring device, and/or plugging device may pierce the proximal side of the tissue wall or may be inserted into existing holes in the tissue wall. In some embodiments, the first anchoring device, second anchoring device, and/or plugging device may be inserted at different points and/or into different holes in the tissue wall. In some embodiments, the first anchoring device, second anchoring device, and plugging device may be inserted at the same point and/or into the same hole in the tissue wall.

At block 606, the process 600 involves passing the first anchoring device, second anchoring device, and plugging device through the distal side of the tissue wall. After piercing the proximal side of the tissue wall, the first anchoring device, second anchoring device, and plugging device may be extended through the tissue wall until they protrude out of the distal side of the tissue wall. In some embodiments, only a portion of the first anchoring device, second anchoring device, and/or plugging device may protrude from the distal side of the tissue wall. For example, a first anchoring device may comprise a suture and an attachment mechanism (e.g., a barb) connected at an end of the suture. In this example, the attachment mechanism and a first portion of the suture may protrude from the distal side of the tissue wall, while a second portion of the suture is situated inside the tissue wall and a third portion of the suture may protrude from the proximal side of the tissue wall. The first portion, second portion, and third portion of the suture may have differing lengths.

At block 608, the process 600 involves securing the plugging device against the distal side of the tissue wall. At least a portion of the plugging device may lay flush against the distal side of the tissue wall (i.e., there may be no space between at least a portion of the plugging device and the tissue wall). The plugging device may be secured against the distal side of the tissue wall as a result of pulling force applied to the first anchoring device, second anchoring device, and/or plugging device. At least a portion of the plugging device may fit and/or be situated between the tissue wall (on a first side of the plugging device) and the first anchoring device and/or second anchoring device (on a second side of the plugging device).

The plugging device may be situated so as to cover at least a portion of at least one hole in the tissue wall. For example, the first anchoring device may pass through a first hole in the tissue wall. To prevent bleeding at the first hole, the plugging device may be configured to block or cover at least a portion of the first hole. The plugging device may be at least partially composed of an absorbent material (e.g., cotton or felt).

At block 610, the process 600 involves attaching and/or connecting the first anchoring device and the second anchoring device outside the distal side of the tissue wall. In some embodiments, an end of the first anchoring device may connect to an end of the second anchoring device. The first anchoring device may comprise a mechanism that may be configured to connect to a mechanism of the second anchoring device. For example, the first anchoring device and the second anchoring device may each comprise a magnet. The magnets may be configured to connect to each other when placed in close proximity. In another example, the first anchoring device may comprise a lasso or loop mechanism that is configured to connect to a hook, balloon, or other mechanism of the second anchoring device.

In certain embodiments, the first anchoring device and/or second anchoring device may connect to the plugging device. For example, the first anchoring device and/or second anchoring device may comprise a barb, hook, corkscrew, and/or other attachment mechanism configured to pierce and/or latch onto the plugging device. In an embodiment, the plugging device may extend from the first anchoring device and/or second anchoring device. Accordingly, attaching the first anchoring device to the second anchoring device may involve connecting the first anchoring device and/or second anchoring device to the plugging device.

Steps of the process 600 may be performed in any order. For example, the plugging device may be inserted first into the tissue wall. When at least a portion of the plugging device is outside the distal side of the tissue wall, the anchoring device may be inserted into the tissue wall and into a portion of the plugging device outside the distal side of the tissue wall. In another example, the anchoring device may be inserted first into the tissue wall. When at least a portion of the anchoring device (e.g., the anchoring mechanism) is outside the distal side of the tissue wall, the plugging device may be inserted into the tissue wall and the anchoring device may be inserted into a portion of the plugging device outside the distal side of the tissue wall. In another example, the anchoring device and the plugging device may be inserted simultaneously or near-simultaneously through the tissue wall.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. An anchoring system comprising:
    a first anchoring device comprising a first attachment mechanism; and
    a second anchoring device comprising a second attachment mechanism and a frame forming a closed loop, the second attachment mechanism forming a covering across the closed loop;
    wherein:
        the second attachment mechanism extends from the frame and does not extend beyond the frame;
        each of the first anchoring device and the second anchoring device is configured to enter a tissue wall at a proximal side of the tissue wall;
        at least a portion of the first anchoring device is configured to exit the tissue wall through a first hole on a distal side of the tissue wall;
        at least a portion of the second anchoring device is configured to exit the tissue wall through a second hole on the distal side of the tissue wall;
        the first attachment mechanism is configured to attach to the second attachment mechanism outside of the distal side of the tissue wall; and
        the second attachment mechanism is configured to at least partially cover the first hole to prevent bleeding.

2. The anchoring system of claim 1, wherein the second attachment mechanism is further configured to fit between at least a portion of the first anchoring device and the distal side of the tissue wall.

3. The anchoring system of claim 1, wherein the second attachment mechanism is at least partially composed of metal and cloth.

4. The anchoring system of claim 1, wherein the first attachment mechanism is configured to pass through and attach to the second attachment mechanism.

5. The anchoring system of claim 1, further comprising a third anchoring device comprising a third attachment mechanism, wherein:
    the third anchoring device is configured to enter the tissue wall at the proximal side of the tissue wall;
    at least a portion of the third anchoring device is configured to exit the tissue wall through a third hole on the distal side of the tissue wall; and
    the third attachment mechanism is configured to attach to the second attachment mechanism outside of the distal side of the tissue wall.

6. The anchoring system of claim 5, wherein the second attachment mechanism is configured to at least partially cover the third hole to prevent bleeding.

7. The anchoring system of claim 1, wherein the second attachment mechanism comprises a metallic mesh.

8. The anchoring system of claim 7, wherein the metallic mesh is overlaid with a cloth.

9. The anchoring system of claim 1, wherein the second anchoring device is configured to encircle the first anchoring device.

10. The anchoring system of claim 1, wherein the closed loop is at a distal end of the second anchoring device.

11. An anchoring system comprising:
    a first anchoring device comprising a first attachment mechanism; and
    a second anchoring device comprising a second attachment mechanism and a frame forming a closed loop, wherein the second attachment mechanism comprises a metallic mesh, and wherein the second attachment mechanism forms a covering across the closed loop;
    wherein:
        the second attachment mechanism extends from the frame and does not extend beyond the frame;
        each of the first anchoring device and the second anchoring device is configured to enter a tissue wall at a proximal side of the tissue wall;
        at least a portion of the first anchoring device is configured to exit the tissue wall through a first hole on a distal side of the tissue wall;
        at least a portion of the second anchoring device is configured to exit the tissue wall through a second hole on the distal side of the tissue wall;
        the first attachment mechanism is configured to pass through and attach to the second attachment mechanism outside of the distal side of the tissue wall; and
        the second attachment mechanism is configured to at least partially cover the first hole to prevent bleeding.

12. The anchoring system of claim 11, wherein the second anchoring device is configured to encircle the first anchoring device.

13. The anchoring system of claim 11, wherein the metallic mesh is overlaid with a cloth.

* * * * *